(12) United States Patent
Gains-Germain et al.

(10) Patent No.: US 10,473,095 B2
(45) Date of Patent: Nov. 12, 2019

(54) SYSTEM FOR PUMP PROTECTION WITH A HYDRAULIC TURBOCHARGER

(71) Applicant: Energy Recovery, Inc., San Leandro, CA (US)

(72) Inventors: Andrea Mary Gains-Germain, San Francisco, CA (US); Jeremy Grant Martin, Oakland, CA (US); Max Shirazi, Emeryville, CA (US); Prem Krish, Foster City, CA (US)

(73) Assignee: ENERGY RECOVERY, INC., San Leandro, CA (US)

( * ) Notice: Subject to any disclaimer, the term of this patent is extended or adjusted under 35 U.S.C. 154(b) by 690 days.

(21) Appl. No.: 14/958,502

(22) Filed: Dec. 3, 2015

(65) Prior Publication Data

US 2016/0160849 A1 Jun. 9, 2016

Related U.S. Application Data

(60) Provisional application No. 62/088,256, filed on Dec. 5, 2014.

(51) Int. Cl.
*F04B 9/10* (2006.01)
*F04B 49/22* (2006.01)
(Continued)

(52) U.S. Cl.
CPC ............ *F04B 9/10* (2013.01); *B01D 53/1425* (2013.01); *B01D 53/18* (2013.01); *C07C 273/04* (2013.01); *F04B 15/04* (2013.01); *F04B 23/02* (2013.01); *F04B 49/22* (2013.01); *F04F 13/00* (2013.01); *B01D 2252/10* (2013.01); *B01D 2257/406* (2013.01); *B01D 2257/504* (2013.01)

(58) Field of Classification Search
CPC ........................................................ F04B 9/10
See application file for complete search history.

(56) References Cited

U.S. PATENT DOCUMENTS

| 6,017,200 A | 1/2000 | Childs et al. |
| 9,440,895 B2 * | 9/2016 | Arluck ............... B01D 53/1462 |

(Continued)

FOREIGN PATENT DOCUMENTS

| WO | 2014/074939 A1 | 5/2014 |
| WO | 2014/074944 A1 | 5/2014 |

OTHER PUBLICATIONS

Michas, Dimitrios. Design of an Energy Recovery Concept for a Small-scale Renewable-driven Reverse Osmosis Desalination System. Oct. 2013. Delft University of Technology. p. 13 (Year: 2013).*

(Continued)

*Primary Examiner* — Abbas Rashid
(74) *Attorney, Agent, or Firm* — Fletcher Yoder, P.C.

(57) ABSTRACT

A system includes a hydraulic energy transfer system configured to exchange pressures between a first fluid and a second fluid. The first fluid is at a higher pressure than the second fluid. The system also includes a high pressure pump configured to increase a pressure of the second fluid. Additionally, the system includes a controller programmed to control one or more valves of the system to selectively route the second fluid to the hydraulic energy transfer system or to the high pressure pump based on an operating condition of the system.

8 Claims, 5 Drawing Sheets

(51) Int. Cl.
*B01D 53/14* (2006.01)
*B01D 53/18* (2006.01)
*F04B 15/04* (2006.01)
*F04B 23/02* (2006.01)
*F04F 13/00* (2009.01)
*C07C 273/04* (2006.01)

(56) References Cited

U.S. PATENT DOCUMENTS

| | | | |
|---|---|---|---|
| 9,604,889 B2* | 3/2017 | Arluck | B01D 53/1456 |
| 2008/0208432 A1* | 8/2008 | Hu | F02B 37/16 |
| | | | 701/103 |
| 2010/0086420 A1 | 4/2010 | Del Pozo Polidoro et al. | |
| 2012/0067825 A1* | 3/2012 | Pique | E21F 3/00 |
| | | | 210/723 |
| 2013/0340430 A1* | 12/2013 | Peters | F02D 29/02 |
| | | | 60/611 |
| 2014/0128655 A1* | 5/2014 | Arluck | C07C 7/11 |
| | | | 585/860 |
| 2014/0128656 A1* | 5/2014 | Arluck | C07C 7/11 |
| | | | 585/860 |
| 2015/0096739 A1* | 4/2015 | Ghasripoor | E21B 43/16 |
| | | | 166/105 |

OTHER PUBLICATIONS

PCT International Search Report and Written Opinion; Application No. PCT/US2015/063866; dated Mar. 16, 2016; 14 pages.

* cited by examiner

SYSTEM FOR PUMP PROTECTION WITH A HYDRAULIC TURBOCHARGER

CROSS-REFERENCE TO RELATED APPLICATION

This application claims priority to and the benefit of U.S. Provisional Application No. 62/088,256, entitled, "SYSTEMS AND METHOD FOR PUMP PROTECTION WITH A HYDRAULIC ENERGY TRANSFER SYSTEM," filed Dec. 5, 2014, the disclosure of which is hereby incorporated in its entirety for all purposes.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

The subject matter disclosed herein relates to rotating equipment, and, more particularly, to systems and methods for handling corrosive fluids with rotating fluid handling equipment.

Pumps, or other fluid displacement systems, may be utilized in a variety of industrial applications to handle or transfer corrosive fluids. In some situations, exposure to corrosive fluids may cause a variety of maintenance issues for the pumps, such as erosion of material, pitting, chipping, spalling, delamination, and so forth. Accordingly, some pumps may be equipped with corrosion resistant materials to help reduce the effects of the corrosive fluids. However, modifications to pump designs and the use of special corrosion resistant materials may increase the overall manufacturing and production costs of the pumps. Furthermore, despite modifications to pump designs and the use of corrosion resistant materials, pumps exposed to corrosive fluids may still have a shorter lifetime and may be expensive to replace, either fully or by components. Accordingly, it may be beneficial to provide systems and methods that protect pumps from corrosive fluids within various industrial applications.

BRIEF DESCRIPTION OF THE DRAWINGS

Various features, aspects, and advantages of the present invention will become better understood when the following detailed description is read with reference to the accompanying figures in which like characters represent like parts throughout the figures, wherein.

DETAILED DESCRIPTION OF SPECIFIC EMBODIMENTS

Figure 1:
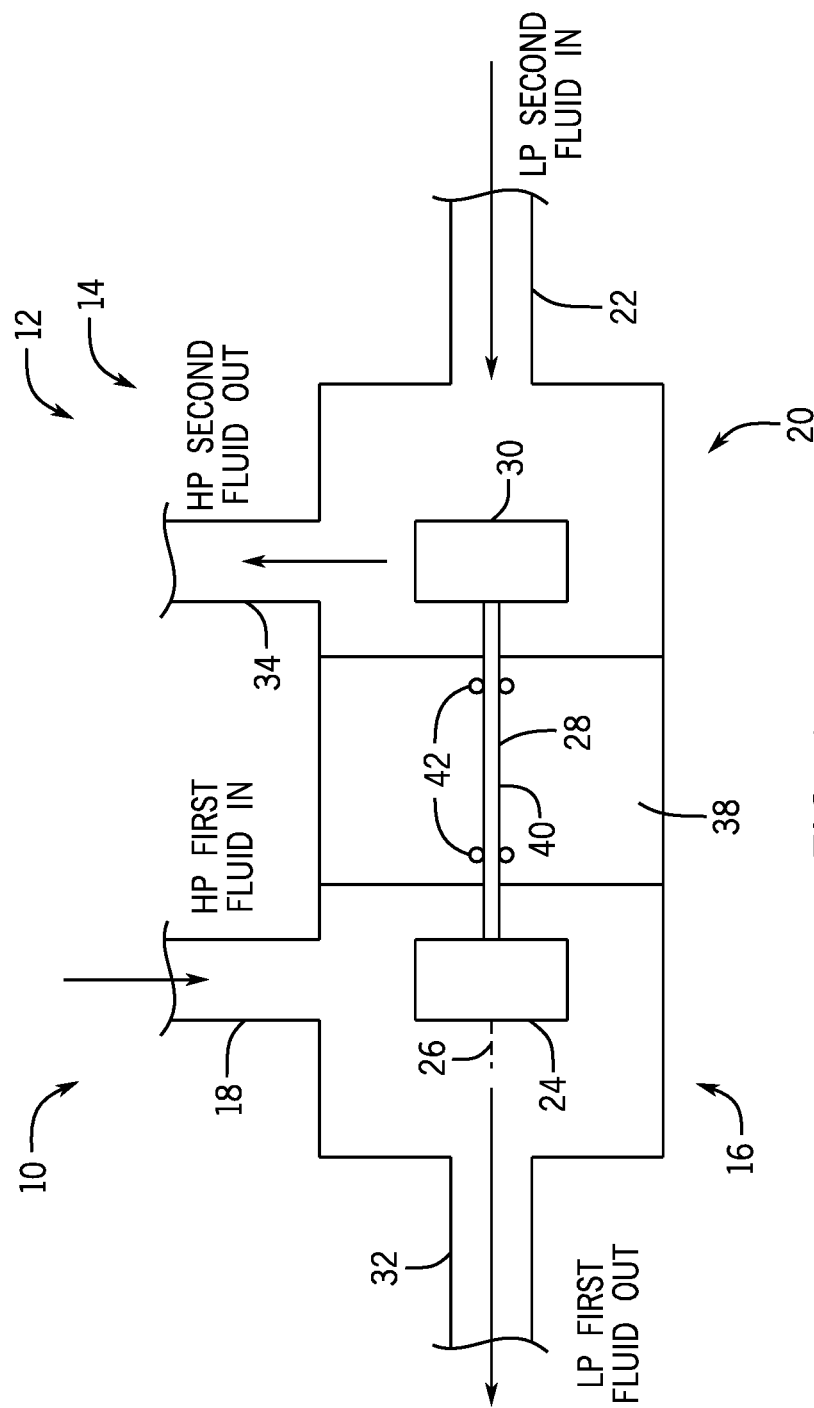
FIG. 1 is a schematic diagram of an embodiment of a system with a hydraulic turbocharger configured to transfer pressures between a first fluid and a second fluid.

One or more specific embodiments of the present invention will be described below. These described embodiments are only exemplary of the present invention. Additionally, in an effort to provide a concise description of these exemplary embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

As noted above, pumps may be utilized in a variety of industrial applications to handle or transfer corrosive fluids. For example, various pumps may be utilized within industrial applications or processes to handle corrosive and/or abrasive fluids, such as, for example, urea, ammonium carbamate, nitric acid, sulfuric acid, ammonium phosphate, calcium phosphate, sodium phosphate, phosphoric acid, hydrofluoric acid, or any other corrosive fluid that may be abrasive (e.g., particle-laden fluids, such as frac fluids), sheer sensitive, viscous, or otherwise challenging to pump. Furthermore, the pumps may be high pressure pumps configured to pump the corrosive fluids to a higher pressure for various applications within the industrial process. In some situations, exposing pumps to corrosive fluids may cause a variety of maintenance issues for the pumps, such as erosion of material, pitting, chipping, spalling, delamination, and so forth. Accordingly, it may be beneficial to provide systems and methods that protect pumps from corrosive fluids within various industrial applications.

As discussed in detail below, the embodiments disclosed herein generally relate to systems and methods for a pump protection system that may be utilized in various industrial applications. The pump protection system may include a hydraulic energy transfer system that transfers work and/or pressure between first and second fluids. In some embodiments, the hydraulic energy transfer system may transfer work and/or pressure between a non-corrosive fluid and a corrosive fluid. In certain embodiments, the hydraulic energy transfer system may transfer work and/or pressure between a first corrosive fluid and a second corrosive fluid. In particular, the hydraulic energy transfer system may be configured to handle the corrosive fluids, thereby protecting various other pumps (e.g., high pressure pumps, carbamate pumps) within the industrial application from having to displace the corrosive fluids and/or otherwise coming into contact with the corrosive fluids. In this manner, the hydraulic energy transfer system minimizes the exposure of the other pumps to the corrosive fluid, thereby reducing wear and/or abrasion to the other pumps and, thus, increasing the life and/or performance of the pumps.

Specifically, the pump protection system may be utilized in a variety of industrial applications, within a variety of plants or processes, or within any industrial setting where a corrosive fluid needs to be pumped or otherwise displaced. For example, the pump protection system may be included within industrial systems such as chemical production systems, urea production systems, ammonium nitrate production systems, polyamide production systems, polyurethane production systems, phosphoric acid production systems, phosphate fertilizer production systems, calcium phosphate fertilizer production systems, oil refining systems, oil extraction systems, fracking systems, petrochemical systems, pharmaceutical systems, or any other industrial systems that include corrosive fluids (e.g., abrasive, sheer sensitive, viscous, or otherwise challenging fluids, etc.).

FIG. 1 is a schematic diagram of an embodiment of an industrial system 10 with a hydraulic energy transfer system 12. The hydraulic energy transfer system 12 may be configured to protect a high pressure pump from a corrosive fluid, an abrasive, particle-laden fluid, or both. In particular, the hydraulic energy transfer system 12 (e.g., a hydraulic turbocharger, rotary isobaric pressure exchanger (IPX), or non-rotating IPX) may be configured to transfer work and/or pressure between a first fluid (e.g., a non-corrosive fluid, a particulate-free fluid, a non-abrasive fluid, a corrosive fluid, an abrasive fluid, a particulate-laden fluid) and a second fluid (e.g., a corrosive fluid, an abrasive, particulate-laden fluid, or both) while reducing or limiting contact (and thus mixing) between the first and second fluids. As noted above, the second fluid may be any corrosive fluid, such as, for example, ammonium carbamate, urea, nitric acid, sulfuric acid, ammonium phosphate, calcium phosphate, sodium phosphate, phosphoric acid, hydrofluoric acid, or any other corrosive fluid that may be abrasive (e.g., particle-laden), sheer sensitive, viscous, or otherwise challenging to pump. In some embodiments, the first fluid may be any non-corrosive fluid and/or particle-free fluid (e.g., water, ammonia, condensate, reflux water, makeup water, etc.). However, in some embodiments, the first fluid may include a corrosive fluid, such as ammonium carbamate and/or urea. In some embodiments, the pressure of the first fluid may be approximately 5% and 2000%, 50% and 1750%, 100% and 1500%, 250% and 1250%, 500% and 1000%, or any other suitable amount greater than the pressure of the second fluid.

In the illustrated embodiment, the hydraulic energy transfer system 12 is a hydraulic turbocharger 14. However, it should be noted that in other embodiments, the hydraulic energy transfer system 12 may be a rotary IPX or non-rotating IPX (e.g., bladder, reciprocating isobaric pressure exchanger). As illustrated, the first fluid (e.g., at high pressure) enters a turbine side 16 of the hydraulic turbocharger 14 through a turbine inlet 18, and the second fluid (e.g., at low pressure) enters a pump side 20 of the hydraulic turbocharger 14 through a pump inlet 22. As the first fluid enters the turbine side 16, the first fluid contacts a first impeller 24, transferring energy from the first fluid to the first impeller 24, which drives rotation of the first impeller 24 about an axis 26 of the hydraulic turbocharger 14. The rotational energy is then transferred through a shaft 28 of the hydraulic turbocharger 14 to a second impeller 30. After transferring energy to the first impeller 24, the first fluid exits the turbine section 16 as a low pressure fluid through a turbine outlet 32. The rotation of the second impeller 30 then increases the pressure of the second fluid entering the pump section 20. Once pressurized, the second fluid exits the pump section 20 as a high pressure fluid through a pump outlet 34.

In certain embodiments, the first fluid may be from a source (e.g., a process fluid, process stream, etc.) within the industrial system 10. It should be noted that in certain situations, the first fluid may be selected such that it does not react with the second fluid when they come in direct contact. Furthermore, the first fluid may be processed or prepared in any form before it is provided to the hydraulic turbocharger 14. For example, in certain embodiments, the first fluid source may be cooled, filtered, or reduced in pressure before it is utilized with the hydraulic turbocharger 14. In some embodiments, the first fluid may be pressurized using a high pressure pump before the first fluid is provided to the hydraulic turbocharger 14. Further, in some embodiments, the first fluid may be a process stream at high pressure. For example, as will be described in more detail below, the first fluid may be a letdown stream of a fluid (e.g., urea) from a vessel (e.g., a high pressure or medium pressure reactor, a tank, a heat exchanger, a stripper, etc.). For example, a letdown stream is typically routed to a pressure-reducing valve (e.g., letdown valve) to reduce the pressure of the fluid in the letdown stream to a desired amount. As used herein, a letdown stream is a fluid that is outputted by a vessel (e.g., a high pressure or medium pressure reactor, a tank, a heat exchanger, stripper, etc.) of the industrial system 10 at first pressure and that is used by a component (e.g., a vessel, a reactor, a dissociation heater and separator, a tank, etc.) of the industrial system 10 at a second pressure that is lower than the first pressure. For example, the first pressure may be approximately 5% and 2000%, 50% and 1750%, 100% and 1500%, 250% and 1250%, 500% and 1000%, or any other suitable percentage greater than the second pressure.

The hydraulic turbocharger 14 may include a wall 38 between the turbine section 16 and the pump section 20 to reduce contact between the first and second fluids. The wall 38 may include an aperture 40 that enables the shaft 28 (e.g., a cylindrical shaft) to extend between the first and second impellers but also minimizes fluid flow. In some embodiments, the hydraulic turbocharger 14 may also include gaskets and/or seals 42 (e.g., annular seals) that may further reduce or block contact between the first and second fluids. Thus, in operation, the hydraulic turbocharger 14 transfers pressures between the first fluid (e.g., a non-corrosive fluid and/or particle-free fluid) and the second fluid (e.g., a corrosive fluid, a particle-laden fluid, or both). In this manner, the hydraulic turbocharger 14 blocks or reduces contact between a high pressure pump of the industrial system 10 and a corrosive and/or particle-laden fluid, thereby reducing wear on the high pressure pump that is typically caused by corrosive fluids. Further, by using a letdown stream (e.g., upstream from the pressure-reducing valve) as the first fluid, the hydraulic energy transfer system 12 (e.g., the hydraulic turbocharger 14) may protect a high pressure pump of the industrial system 10 from a corrosive and/or particle-laden fluid, while reducing energy consumption of the industrial system 10, reducing operating costs of the industrial system 10, and increasing process efficiencies of the industrial system 10 by recycling otherwise wasted pressure of the letdown stream.

In certain embodiments, the hydraulic turbocharger 14 may be constructed of materials (e.g., bearing materials) with a sufficient hardness to reduce or minimize wear, abrasion, and/or erosion that may result from contact with corrosive fluids. For example, the hydraulic turbocharger 14 may have a bearing surface hardness between approximately 1000 HV30 hardness (e.g., on the Vickers hardness scale) to 2000 HV30 hardness or more. Further, as will be described in more detail below, in certain embodiments, the hydraulic turbocharger 14 may include a bearing lubrication system and/or a condensate flush to reduce or minimize wear and/or to flush particles (e.g., carbamate crystals) from the hydraulic turbocharger 14.

Figure 2:
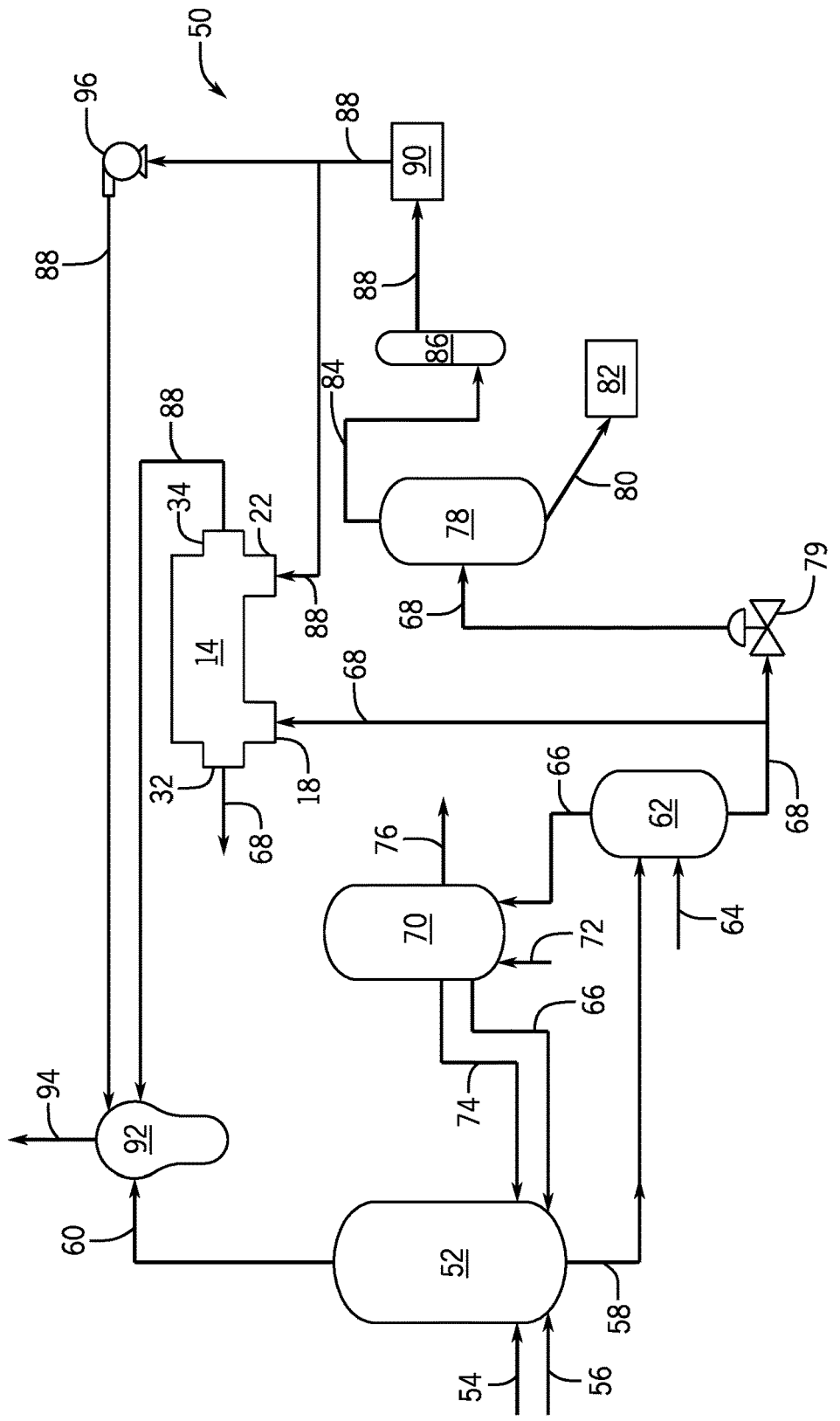
FIG. 2 is a schematic diagram of an embodiment of a urea synthesis system including the hydraulic turbocharger of FIG. 1, where the hydraulic turbocharger is configured to pressurize an ammonium carbamate stream.

FIG. 2 is a schematic diagram of an embodiment of a urea synthesis system 50 including the hydraulic turbocharger 14. It should be appreciated that, for simplicity, the illustrated embodiment of the urea synthesis system 50 may not depict all of the components of a urea synthesis system (e.g., evaporation components, desorption and hydrolysis components, fluid bed granulation components, etc.). Urea is synthesized by reacting carbon dioxide and ammonia at a high temperature and pressure. Specifically, carbon dioxide and ammonia react to produce ammonium carbamate (e.g., a corrosive fluid), which is dehydrated to form urea. As illustrated, the urea synthesis system 50 includes a reactor 52 that receives a first carbon dioxide 54 and a first ammonia stream 56 (e.g., liquid ammonia), and a first urea synthesis stream 58 may exit from the bottom of the reactor 52. The first urea synthesis stream 58 may include urea, carbon dioxide, ammonium carbamate, water, and/or unreacted ammonia. The urea synthesis reaction in the reactor 52 may also produce a first gas stream 60 that may contain inert gas, ammonia, carbon dioxide, and water. To increase the purity and yield of urea, stripping and condensing processes may be used, as will be described in more detail below.

In particular, the first urea synthesis stream 58 may be fed to a high pressure heat exchanger (e.g., stripper) 62. A second carbon dioxide stream 64 (e.g., at a high pressure that is substantially equal to the pressure of the first urea synthesis stream 58) may also be fed to the stripper 62. It should be noted that in certain embodiments, the second carbon dioxide stream 64, which may include air, may be compressed using a carbon dioxide compressor and processed using a hydrogen removal reactor before the second carbon dioxide stream 64 is fed to the stripper 62. Contact with the second carbon dioxide stream 64 may separate the unreacted ammonium carbamate from the first urea synthesis stream 58. The stripper 62 may output a second gas stream 66, which may include ammonia, carbon dioxide, and water, and a second urea synthesis stream 68, which may include urea and ammonium carbamate.

The second gas stream 66 from the stripper 62 may be fed to a high pressure carbamate condenser (HPCC) 70, where it is condensed and recycled back to reactor 52. In certain embodiments, a second ammonia stream 72 may also be fed to the HPCC 70, which may react with the carbon dioxide in the gas mixture stream 66 to produce a third urea synthesis stream 74. The second gas stream 66 and the third urea synthesis stream 74 may be fed to the reactor 52 to increase the purity and yield of urea. The HPCC 70 may also produce a condensate stream 76 (e.g., steam or water), which may be used by other components of the urea synthesis system 50, as will be described in more detail below.

The second urea synthesis stream 68 from the stripper 62 may be fed to a dissociation heater and separator 78, which may separate any remaining ammonium carbamate, water, ammonia, or inert gases from urea. In some embodiments, the second urea synthesis stream 68 may first pass through a letdown valve 79, which may reduce the pressure of the second urea synthesis stream 68. The dissociation heater and separator 78 may output a third urea synthesis stream 80 that may be stored in a flash tank 82. It should be noted that the third urea synthesis stream 80 stored in the flash tank 82 may be further processed using evaporation processes, desorption and hydrolysis processes, and/or fluid bed granulation processes. The dissociation heater and separator 78 may also output a third gas stream 84, which may be fed to a low pressure carbamate condenser 86, where ammonium carbamate in the third gas stream 84 may be condensed and separated from the third gas stream 84. An ammonium carbamate stream 88 from the low pressure carbamate condenser 86 may be fed to a level tank 90 for low pressure ammonium carbamate.

As noted above, the reactor 52 outputs the first gas stream 60 that may contain inert gas, ammonia, carbon dioxide, and water. To minimize emissions, the first gas stream 60 may be washed in a high pressure scrubber 92 using a high pressure absorption medium to absorb ammonia and carbon dioxide. As such, the scrubber 92 may output a fourth gas stream 94 that includes mainly inert gases and a minimal amount of ammonia and carbon dioxide. In particular, the scrubber 92 may utilize recycled high pressure ammonium carbamate as the absorption medium. Specifically, the recycled ammonium carbamate may be sourced from the level tank 90 that stores the ammonium carbamate stream 88 at low pressure. The ammonium carbamate stream 88 from the level tank 90 may be pressurized using a high pressure carbamate pump 96 to a high pressure that is suitable for scrubbing the first gas stream 60 in the scrubber 92. However, as described in detail above, ammonium carbamate is a corrosive fluid that may cause wear and abrasion to the high pressure carbamate pump 96. As such, exposure to ammonium carbamate may reduce the performance and/or life of the high pressure carbamate pump 96, which increases the downtime and capital costs of the urea synthesis system 50 associated with replacing and/or repairing the high pressure carbamate pump 96.

Accordingly, the urea synthesis system 50 includes the hydraulic turbocharger 14 to reduce the exposure of the high pressure carbamate pump 96 to ammonium carbamate. In particular, the hydraulic turbocharger 14 may be configured to transfer pressure from the second urea synthesis stream 68 to the ammonium carbamate stream 88. Specifically, the hydraulic turbocharger 14 may receive the second urea synthesis stream 68 at high pressure in the turbine inlet 18 and the ammonium carbamate stream 88 at low pressure in the pump inlet 22, and may output the second urea synthesis stream 68 at low pressure via the turbine outlet 32 and the ammonium carbamate stream 88 at high pressure via the pump outlet 34. Accordingly, the hydraulic turbocharger 14 may reduce wear to the high pressure carbamate pump 96, which may reduce the downtime and capital costs associated with replacing and/or repairing the high pressure carbamate pump 96 and may reduce the energy costs of the urea synthesis system 50.

Figure 3:
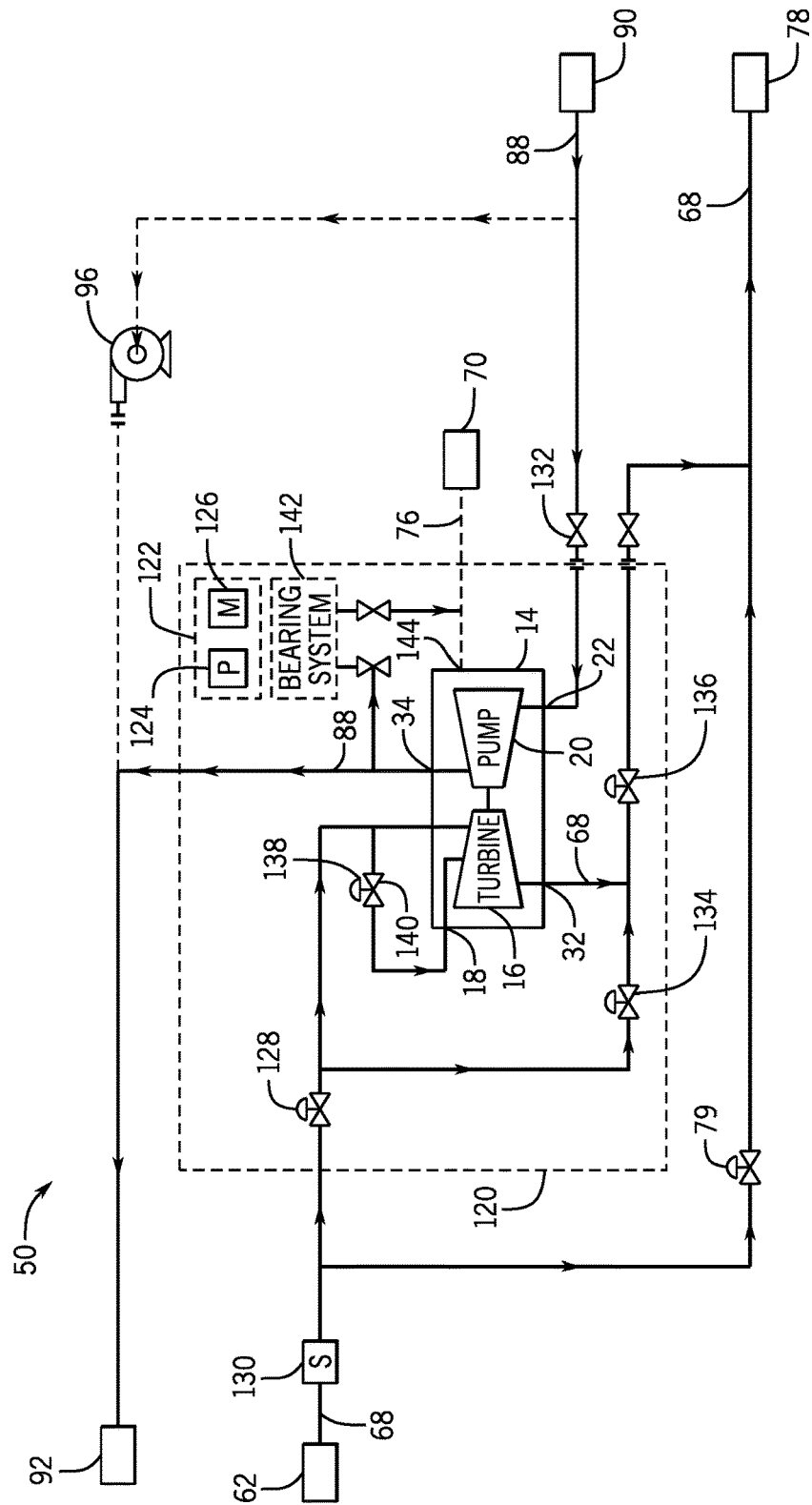
FIG. 3 is a schematic diagram of an embodiment of the urea synthesis system of FIG. 2 including the hydraulic turbocharger of FIG. 1 and a control system configured to selectively route the ammonium carbamate stream to the hydraulic turbocharger or to a high pressure pump.

FIG. 3 illustrates a schematic diagram of an embodiment of the urea synthesis system 50 that includes a turbocharger system 120 including the hydraulic turbocharger 14 and that includes the high pressure carbamate pump 96, which may be utilized during abnormal conditions (e.g., unstable conditions) of the urea synthesis process, such as during start up and shut down. For example, the flow of the second urea synthesis stream 68 and/or the flow of the ammonium carbamate stream 88 may vary during start up and shut down, so it may be desirable to utilize the high pressure carbamate pump 96 to pressurize the ammonium carbamate stream 88. Accordingly, in some embodiments, the urea synthesis system 50 may utilize the hydraulic turbocharger 14 to pressurize the ammonium carbamate stream 88 during stable process conditions (e.g., not during start up and shut down). Further, in certain embodiments, the urea synthesis system 50 may utilize the high pressure carbamate pump 96 to pressurize the ammonium carbamate stream 88 during start up and/or shut down of the industrial system 10. Stable or steady-state process conditions may be present for approximately 90 percent to 99 percent of the running time. The second urea synthesis stream 68 may have a pressure between approximately 10000 kPa and 20000 kPa, 12000 kPa and 18000 kPa, 13000 kPa and 15000 kPa, or any other suitable range. Additionally, the ammonium carbamate stream 88 may have a pressure between approximately 10 kPa and 2000 kPa, 100 kPa and 1000 kPa, 200 kPa and 800 kPa, or 300 kPa and 500 kPa, or any other suitable range.

Accordingly, to enable the urea synthesis system 50 to switch between the hydraulic turbocharger 14 and the high pressure carbamate pump 96, the urea synthesis system 50 and the turbocharger system 120 may include one or more valves to direct the process streams of the urea synthesis system 50. Additionally, the turbocharger system 120 may include a control system 122 (e.g., a controller) including one or more processors 124 and one or more memory devices 126 (e.g., tangible, non-transitory, computer-readable memory devices). The processor 124 may be configured to read and execute instructions stored on the memory device 126 for implementing the techniques described herein. Further, as will be described in more detail below, the processor 124 may be configured to utilize information (e.g., feedback) from one or more sensors (e.g., flow sensors, pressure sensors, temperature sensors, composition sensors, etc.) of the urea synthesis system 50 to determine whether abnormal (e.g., unstable) conditions, start up conditions, shut down conditions, or stable conditions are present and to control the actuation of one or more valves (e.g., open or close the valves) of the urea synthesis system 50 based on a detected condition of the industrial system 10. In particular, the processor 124 may control the one or more valves to switch between operation of the hydraulic turbocharger 14 and operation of the high pressure carbamate pump 96 based on a detected condition of the industrial system 10. For example, the processor 124 may control the one or more valves to route the first fluid and/or the second fluid to the hydraulic turbocharger 14 when a stable condition is detected, and the processor 124 may control the one or more valves to reduce, block, or stop flow of the first fluid and/or the second fluid to the hydraulic turbocharger 14 when an abnormal (e.g., unstable) condition is detected. In some embodiments, the processor 124 may route the second fluid to the high pressure carbamate pump 96 when an abnormal (e.g., unstable) condition is detected.

In particular, the turbocharger system 120 may include a throttle valve 128 (e.g., a level control valve (LCV), an actuated valve) downstream of the second urea synthesis stream 68 and upstream of the hydraulic turbocharger 14 (e.g., upstream of a first fluid inlet of the hydraulic turbocharger 14, upstream of the turbine inlet 18). The urea synthesis system 50 and/or the turbocharger system 120 may also include one or more sensors 130 (e.g., pressure sensors, flow meters, temperature sensors, composition sensors, optical sensors, vibration sensors, or a combination thereof) that are configured to generate feedback (e.g., pressure feedback, flow rate feedback, temperature feedback, vibration feedback, composition feedback, or a combination thereof) relating to the second urea synthesis stream 68. For example, the one or more sensors 130 may be disposed downstream of the stripper 62 and upstream of the hydraulic turbocharger 14. In some embodiments, the one or more sensors 130 may be disposed upstream of the letdown valve 79. The processor 124 may be configured to analyze feedback from the one or more sensors 130, feedback from sensors disposed about other locations of the urea synthesis system 50, other feedback or information relating to the operation of the urea synthesis system 50, such as the flow rate of the first urea stream 58 outputted by the reactor 52 relative to the a design point flow (e.g., the originally designed flow) from the reactor 52, a percentage of the design point flow (e.g., the percentage of the flow rate of the first urea stream 58 outputted by the reactor 52 relative to the design point flow from the reactor 52), the design pressure of the reactor 52 (e.g., the operating pressure of the reactor 52 relative to the design pressure), etc. In some embodiments, the processor 124 may determine a flow rate, temperature, and/or pressure of the second urea synthesis stream 68 based on feedback from the one or more sensors 130. Further, the one or more sensors 130 may be configured to generate feedback (e.g., pressure feedback, flow rate feedback, temperature feedback, etc.) related to the operating pressure of the reactor 52, the flow rate of the first urea stream 58, and so forth.

Further, the processor 124 may utilize the received feedback and/or information stored in the memory device 126 to determine whether the conditions of the urea synthesis system 50 are stable or abnormal (e.g., unstable, a start-up condition, a shut-down condition, etc.). For example, the memory device 126 may be configured to store a predetermined minimum pressure threshold and/or a predetermined minimum flow threshold for the second urea synthesis stream 68 associated with stable operating conditions, such as the pressure ranges for the second urea synthesis stream 68 described above. Accordingly, the processor 124 may compare the determined pressure and/or flow rate of the second urea synthesis stream 68 to the predetermined minimum pressure threshold and/or the predetermined minimum flow threshold, respectively, to determine the operating condition of the urea synthesis system 50. For example, the processor 124 may detect a stable operating condition in response to a determination that the pressure of the urea synthesis stream 68 is greater than the predetermined minimum pressure threshold, a determination that the flow rate of the urea synthesis stream 68 is greater than the predetermined minimum flow threshold, or both. Further, the processor 124 may detect an abnormal (e.g., unstable) operating condition (e.g., a start-up condition, a shut-down condition, etc.) in response to a determination that the pressure of the urea synthesis stream 68 is less than the predetermined minimum pressure threshold, a determination that the flow rate of the urea synthesis stream 68 is less than the predetermined minimum flow threshold, or both. Further, in other embodiments, the processor 124 may be configured to analyze trends in the feedback from the sensors 130 to determine when the operating conditions are abnormal (e.g., unstable) or stable. For example, the processor 124 may determine that the operating conditions are stable if the sensor values (e.g., pressure values, flow rate values, etc.) remain generally stable after a predetermined amount of time. Additionally, the processor 124 may be configured to determine that the operating conditions are abnormal in response to a spike in sensors values (e.g., a value that exceeds a threshold).

Additionally, in some embodiments, the memory device 126 may be configured to store a predetermined minimum threshold percentage of the design point flow of the urea synthesis system 50. For example, the predetermined minimum threshold percentage may be between approximately 30 percent and 100 percent, 40 percent and 95 percent, 50 percent and 90 percent, or any other suitable range. In some embodiments, the processor 124 may determine the percentage of the flow rate of the first urea stream 58 outputted by the reactor 52 relative to a predetermined design point flow, and the processor 124 may determine that the operating condition is stable if the percentage is greater than the predetermined minimum threshold percentage and may determine that the operating condition is abnormal if the percentage is less than the predetermined minimum threshold percentage. Further, the memory device 126 may be configured to store a predetermined minimum threshold for the design pressure of the reactor 52. For example, the predetermined minimum threshold may be between approximately 50 bar and 300 bar, 75 bar and 250 bar, 100 bar and 200 bar, or any other suitable range. In some embodiments, the processor 124 may determine that the operating condition is stable if the operating pressure of the reactor 52 is greater than the predetermined minimum threshold for the design pressure and may determine that the operating condition is abnormal if the operating pressure of the reactor 52 is less than the predetermined minimum threshold of the design pressure.

The processor 124 may independently control one or more valves of the urea synthesis system 50 based on the detected operating condition. For example, the processor 124 may control one or more valves to enable flow of the first fluid and/or flow of the second fluid to the hydraulic turbocharger 14 in response to a determination that the operating condition is stable. In some embodiments, the processor 124 may control one or more valves to reduce, block, or stop flow of the first fluid and/or the second fluid to the hydraulic turbocharger in response to a determination that the operating condition is abnormal (e.g., a start-up condition, a shut-down condition, etc.). Further, in certain embodiments, the processor 124 may control one or more valves to route the second fluid to the high pressure carbamate pump 96 in response to a determination that the operating condition is abnormal. For example, in some embodiments, the processor 124 may selectively cause a throttle valve 128 to close in response to a determination that the conditions are abnormal and may selectively cause the throttle valve 128 to open in response to a determination that the conditions are stable. In some embodiments, the throttle valve 128 may receive the second urea synthesis stream 68 and may be disposed upstream of the hydraulic turbocharger 14. Further, in some embodiments, the throttle valve 128 may be in parallel with the letdown valve 79.

Further, the urea synthesis system 50 may include a valve 132 (e.g., a gate valve, a bypass valve, a level control valve, a flow control valve, etc.) downstream of the ammonium carbamate stream 88 from the level tank 90 and upstream of the hydraulic turbocharger 14 (e.g., upstream of a second fluid inlet of the hydraulic turbocharger 14, upstream of the pump inlet 22). The processor 124 may also be configured to selectively cause the valve 132 to open or close based at least in part upon the determination that the operating conditions are stable or abnormal. In particular, if the processor 124 determines that the conditions are abnormal, the processor 124 may selectively cause the valve 132 to close to bypass the hydraulic turbocharger 14. Alternatively, if the processor 124 determines that the conditions are stable, the processor 124 may selectively cause the valve 132 to open to direct the ammonium carbamate stream 88 to the hydraulic turbocharger 14.

As such, when the processor 124 determines that the operating conditions are abnormal, the second urea synthesis stream 68 may be routed to the letdown valve 79 and may not pass through the hydraulic turbocharger 14. Additionally, for abnormal conditions, the ammonium carbamate stream 88 may be pressurized and routed to the high pressure scrubber 92 via the high pressure carbamate pump 96 and may not pass through the hydraulic turbocharger 14. Further, when the processor 124 determines that the operating conditions are stable, the ammonium carbamate stream 88 may be pressurized via the hydraulic turbocharger 14 and may not pass through the high pressure carbamate pump 96. Additionally, for stable conditions, the second urea synthesis stream 68 may be depressurized via the hydraulic turbocharger 14 and may not pass through the letdown valve 79. However, in some embodiments, the second urea synthesis stream 68 may be routed through and depressurized using both the hydraulic turbocharger 14 and the letdown valve 79.

Additionally, the turbocharger system 120 may include one or more valves. In particular, the turbocharger system 120 may include a bypass valve 134, a letdown valve 136, and an auxiliary valve 138. These valves (e.g., via controlled actuators) may be actuated by the processor 124, and in particular, may be actuated by the processor 124 to adjust the percentage of the flow of the second urea synthesis stream 68 that enters the turbine inlet 18 and is depressurized by the hydraulic turbocharger 14. For example, if the processor 124 determines (e.g., based on feedback from the sensors 130) that the second urea synthesis stream 68 has more energy (e.g., pressure) than needed by the hydraulic turbocharger 14, the processor 124 may selectively control the valves 134, 136, and 138 such that a percentage of the flow of the second urea synthesis stream 68 is routed to the bypass valve 134 and the letdown valve 136 and does not pass through the hydraulic turbocharger 14. The letdown valve 136 may decrease the pressure of the second urea synthesis stream 68. Additionally, the letdown valve 136 may be downstream of the turbine outlet 32, and as such, may also decrease the pressure of the second urea synthesis stream 68 exiting the turbine outlet 32. The auxiliary valve 138 may control the flow of the urea synthesis stream 68 to an auxiliary nozzle 140 of the hydraulic turbocharger 14. In particular, the flow to the auxiliary nozzle 140 may vary based on the degree of openness of the auxiliary valve 138, where the minimum flow to the turbine inlet 18 is when the auxiliary valve 138 is fully closed and the maximum flow to the turbine inlet 18 is when the auxiliary valve 138 is fully open. Thus, controlling the auxiliary valve 138 (e.g., via the processor 124) enables the functionality of a variable geometry turbine 16.

As illustrated, the turbocharger system 120 may also include a bearing lubrication system 142. The bearing lubrication system 142 may be configured to receive the high pressure ammonium carbamate stream 88 exiting the pump outlet 34, to filter and/or process the high pressure ammonium carbamate stream 88 using one or more filters or treatment components of the bearing lubrication system 142, and to route the filtered ammonium carbamate stream 88 to a bearing inlet 144 of the hydraulic turbocharger 14. The ammonium carbamate may be corrosive to the bearing system of the hydraulic turbocharger 14, and as such, the condensate stream 76 from the HPCC 70 may also be provided as a bearing fluid for the hydraulic turbocharger 14 and/or may be provided to the hydraulic turbocharger 14 to flush out any particles, such as carbamate crystals from the ammonium carbamate.

Figure 4:
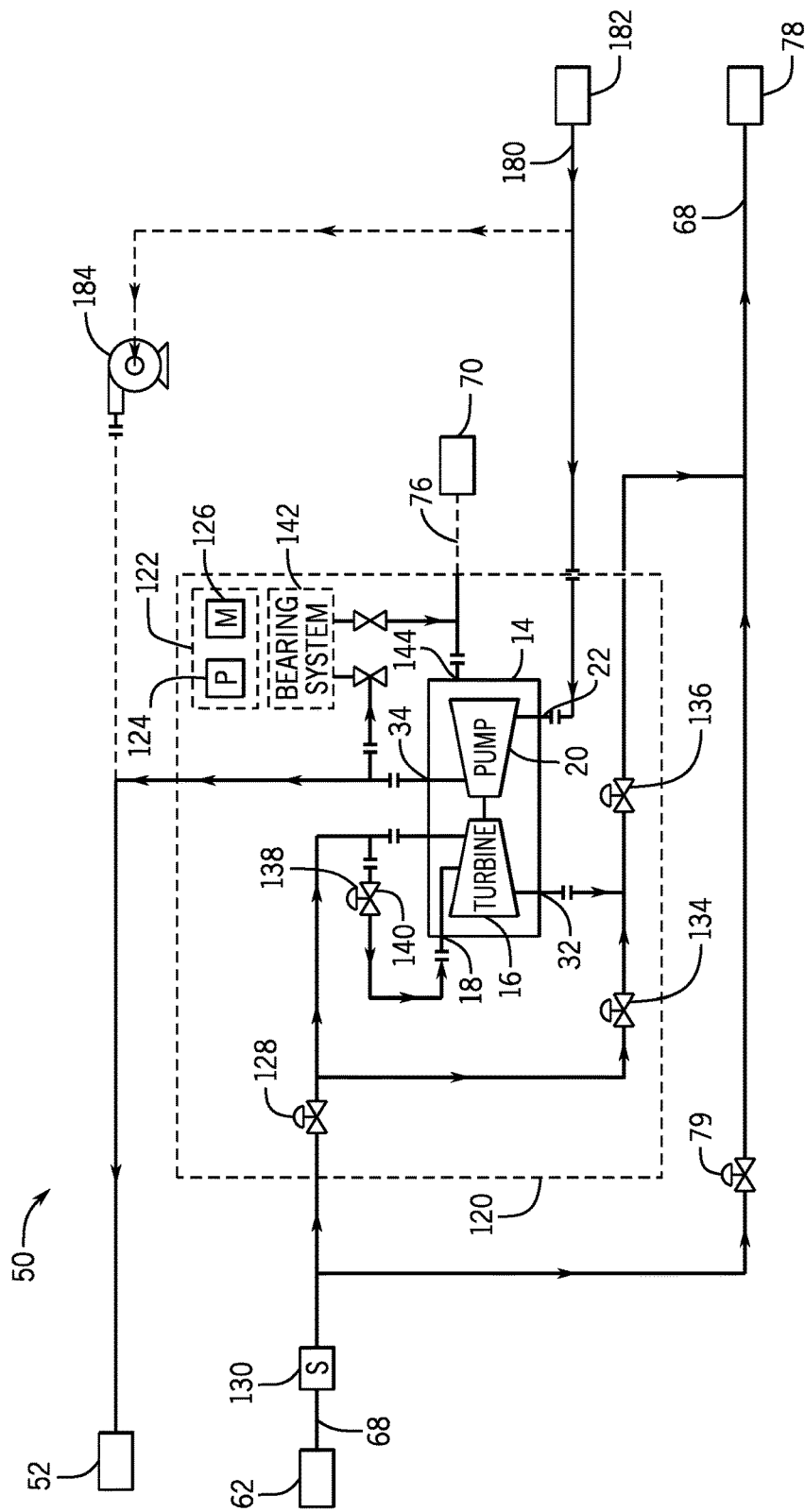
FIG. 4 is a schematic diagram of an embodiment of the urea synthesis system of FIG. 2 including the hydraulic turbocharger of FIG. 1, wherein the hydraulic turbocharger is configured to pressurize a process stream of the urea synthesis system.

While the embodiment illustrated in FIG. 3 relates to the ammonium carbamate stream 88, the disclosed techniques may also be used to pressurize other process streams of the urea synthesis system 50 or of other industrial systems. For example, FIG. 4 illustrates an embodiment of the urea synthesis system 50 including the hydraulic turbocharger 14, in which the hydraulic turbocharger 14 is configured to receive and pressurize a process stream 180 from a storage tank 182. The process stream 180 may be any suitable process stream from the urea synthesis system 50 that may be stored at a low pressure and may be fed to the reactor 52 (or another vessel or component of the urea synthesis system 50) at a higher pressure. In certain embodiments, the process stream 180 may be corrosive and/or particle-laden. Additionally, the urea synthesis system 50 may be configured to utilize other high pressure pumps rather than the high pressure carbamate pump 96. For example, a high pressure ammonia pump 184 may be used to pressurize the process stream 180 and route the process stream 180 to the reactor 52 when the processor 124 determines that the operating conditions are abnormal.

Figure 5:
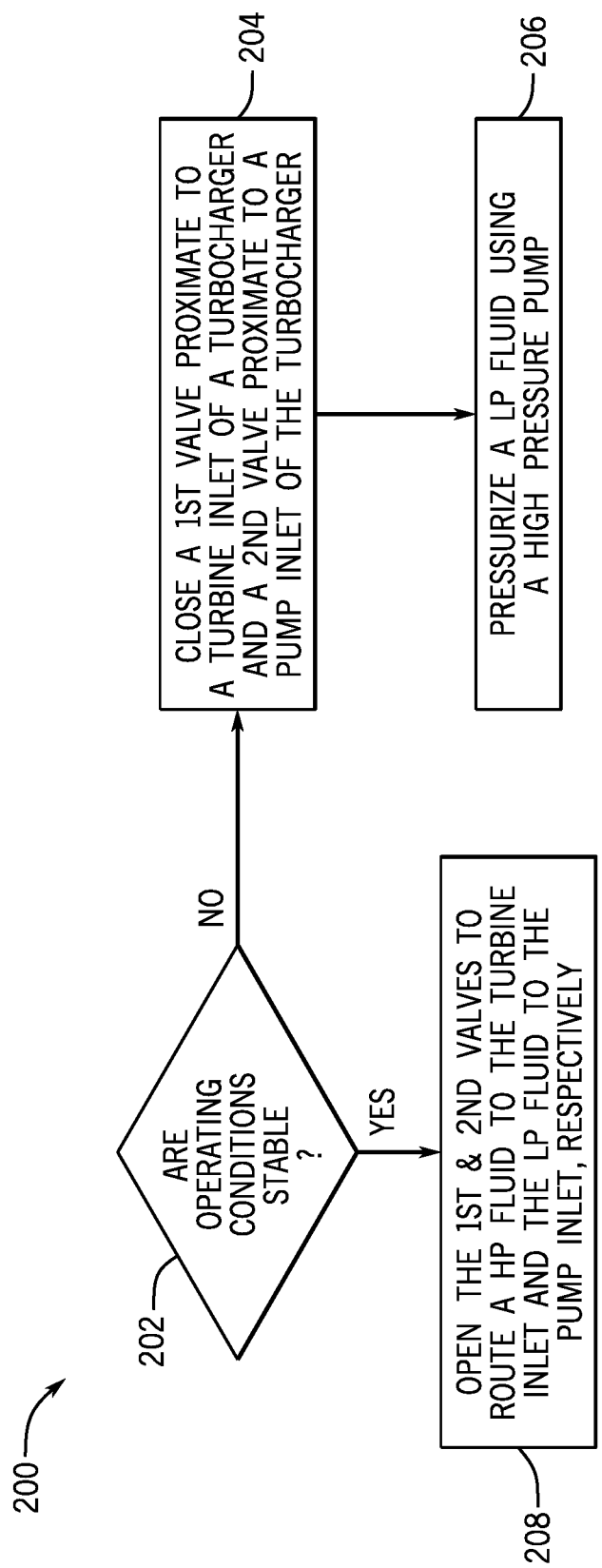
FIG. 5 is a process flow diagram of a method for selectively routing a fluid to a hydraulic turbocharger or to a high pressure pump of an industrial system.

FIG. 5 illustrates a flow diagram of a method 200 for operating a system (e.g., the industrial system 10, the urea synthesis system 50, etc.) including a hydraulic energy transfer system (e.g., the hydraulic energy transfer system 12, the hydraulic turbocharger 14, etc.). The method 200 includes determining whether operating conditions of the system are stable (block 202). As described in detail above, the processor 124 may determine whether the conditions of the system are stable or abnormal based at least in part upon feedback received from one or more sensors of the system (e.g., the sensors 130), which may relate to a pressure and/or flow of a process stream of the system (e.g., the second urea synthesis stream 68), a percentage of a design point flow of the system, a design pressure of a reactor of the system, etc. Further, the processor 124 may determine whether the conditions are stable or abnormal based at least in part upon information stored in the memory device 126. For example, the processor 124 may compare feedback from the sensors 130 to thresholds stored in the memory device 126. In some embodiments, the processor 124 may receive an input indicating the operating condition of the system. For example, the processor 124 may receive the input from another component (e.g., controller) of the system. In some embodiments, the processor 124 may receive the input from an input device that is coupled to the processor 124 and configured to receive an input from a user. For example, the input device may include one or more buttons, one or more switches, a keyboard, a mouse, a touch-screen display, or a combination thereof.

If the conditions are not stable, the method 200 may include closing a first valve (e.g., the throttle valve 128) proximate to the turbine inlet 18 of the hydraulic turbocharger 14 and closing a second valve (e.g., the valve 132) proximate to the pump inlet 22 of the hydraulic turbocharger 14 (block 204). Closing the first valve may block a first fluid (e.g., a high pressure non-corrosive fluid, the second urea synthesis stream 68) from entering the turbine inlet 18 and a second fluid (e.g., a low pressure corrosive fluid, the ammonium carbamate stream 88, the process stream 180) from entering the pump inlet 22. Additionally, the method 200 may include pressuring a low pressure fluid (e.g., the second fluid) using a high pressure pump (block 206). If the conditions are stable, the method 200 may include opening the first and second valves to route a high pressure fluid (e.g., the first fluid) to the turbine inlet 18 and the low pressure fluid (e.g., the second fluid) to the pump inlet 22, respectively (block 208).

It should be noted that various components of the industrial system 10 and/or the urea synthesis system 50 may be connected via wired or wireless connections. For example, the control system 122 may be connected to the valves 79, 128, 132, 134, 136, and/or 138, the auxiliary nozzle 140, and/or the sensors 130 via wired and/or wireless connections. Further, the control system 122 may include the one or more processors 124, which may include microprocessors, microcontrollers, integrated circuits, application specific integrated circuits, and so forth. Additionally, the control system 122 may include the one or more memory devices 126, which may be provided in the form of tangible and non-transitory machine-readable medium or media (such as a hard disk drive, etc.) having instructions recorded thereon for execution by a processor (e.g., the processor 124) or a computer. The set of instructions may include various commands that instruct the processor 124 to perform specific operations such as the methods and processes of the various embodiments described herein. The set of instructions may be in the form of a software program or application. The memory devices 126 may include volatile and non-volatile media, removable and non-removable media implemented in any method or technology for storage of information such as computer-readable instructions, data structures, program modules or other data. The computer storage media may include, but are not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other suitable storage medium. Further, the control system 122 may include or may be connected to a device (e.g., an input and/or output device) such as a computer, laptop computer, monitor, cellular or smart phone, tablet, other handheld device, or the like that may be configured to receive data and show the data on a display of the device.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A system, comprising:
    a hydraulic turbocharger configured to exchange pressures between a first fluid and a second fluid, wherein the first fluid is at a higher pressure than the second fluid;
    a high pressure pump configured to increase a pressure of the second fluid, wherein the high pressure pump comprises an outlet for the second fluid that is not fluidly coupled to the hydraulic turbocharger; and
    a controller programmed to control one or more valves of the system to selectively route the second fluid to the hydraulic turbocharger or to the high pressure pump based on an operating condition of the system; a letdown valve; wherein the controller is programmed to control the one or more valves of the system to selectively route the first fluid to the hydraulic turbocharger or to the letdown valve based on the operating condition of the system; wherein the controller is programmed to control the one or more valves to route the first fluid to the hydraulic turbocharger when the operating condition is a stable operating condition and to route the first fluid to the letdown valve when the operating condition is a start-up condition or a shut-down condition.

2. The system of claim 1, wherein the controller is programmed to control the one or more valves to route the second fluid to the hydraulic turbocharger when the operating condition is a stable operating condition and to route the second fluid to the high pressure pump while blocking flow of the second fluid to the hydraulic turbocharger when the operating condition is the start-up condition or the shut-down condition.

3. The system of claim 1, comprising one or more sensors configured to generate feedback relating to the operating condition, wherein the controller is programmed to receive the feedback from the one or more sensors and to determine the operating condition of the system based on the feedback.

4. The system of claim 3, wherein the one or more sensors comprise a first sensor configured to generate feedback relating to a pressure, a flow rate, or both of the first fluid.

5. The system of claim 4, wherein the controller is programmed to determine that the operating condition is stable in response to a determination that the pressure of the first fluid is greater than a pressure threshold, a determination that the flow rate of the first fluid is greater than a flow threshold, or both.

6. The system of claim 5, wherein the controller is programmed to determine that the operating condition is the start-up condition or the shut-down condition in response to a determination that the pressure of the first fluid is less than the pressure threshold, a determination that the flow rate of the first fluid is less than the flow threshold, or both.

7. The system of claim 1, wherein the first fluid comprises urea, ammonium carbamate, or both, and the second fluid comprises ammonium carbamate.

8. The system of claim 1, wherein the first fluid comprises a letdown fluid of the system.

* * * * *